United States Patent
Schendel

(10) Patent No.: US 6,589,250 B2
(45) Date of Patent: Jul. 8, 2003

(54) MAXILLARY DISTRACTION DEVICE

(76) Inventor: Stephen A. Schendel, 1001 Hermosa Way, Menlo Park, CA (US) 94025

( * ) Notice: Subject to any disclaimer, the term of this patent is extended or adjusted under 35 U.S.C. 154(b) by 0 days.

(21) Appl. No.: 09/988,529

(22) Filed: Nov. 20, 2001

(65) Prior Publication Data

US 2003/0097137 A1 May 22, 2003

(51) Int. Cl.[7] .................................................. A61F 2/36
(52) U.S. Cl. ........................... 606/105; 606/57; 606/71; 433/7
(58) Field of Search ............................ 606/105, 53, 54, 606/55, 57, 60, 69, 70, 71, 86; 433/7

(56) References Cited

U.S. PATENT DOCUMENTS

| | | | |
|---|---|---|---|
| 1,504,942 A | | 8/1924 | Comegys |
| 2,362,741 A | | 2/1944 | Berke |
| 4,676,745 A | * | 6/1987 | Zurita ........................... 433/6 |
| 5,147,358 A | | 9/1992 | Remmler |
| 5,700,263 A | | 12/1997 | Schendel |
| 5,807,382 A | | 9/1998 | Chin |
| 5,885,283 A | | 3/1999 | Gittleman |
| 5,885,289 A | | 3/1999 | Muller |
| 5,885,290 A | * | 3/1999 | Guerrero et al. ............... 606/71 |
| 6,129,728 A | | 10/2000 | Schumacher |
| 6,139,316 A | | 10/2000 | Sachdeva |
| 6,187,004 B1 | | 2/2001 | Fearon |
| 6,267,589 B1 | * | 7/2001 | Farzin-Nia et al. ............ 433/7 |
| 6,358,255 B1 | * | 3/2002 | Testa .......................... 606/105 |

* cited by examiner

Primary Examiner—Pedro Philogene
(74) Attorney, Agent, or Firm—Baker Botts L.L.P.

(57) ABSTRACT

A device for maxillary jawbone and dentition expansion and/or retraction is configured for mounting within the mouth and connects the right and left halves of the skull. The maxillary distraction device includes at least two implantable anchors configured to be implanted in the maxillary bones of the skull on opposite sides of a midline of the skull. A facebow having two posterior ends is connectable to the implantable anchors and is configured to extend from the maxillary regions entirely within the mouth across the midline of the skull. The facebow has at least one expandable section for bone lengthening. The facebow is connected to the anchors and is lengthen periodically to lengthen the maxillary bones. The facebow may provide horizontal, vertical, and transverse distraction.

22 Claims, 4 Drawing Sheets

MAXILLARY DISTRACTION DEVICE

FIELD OF THE INVENTION

The invention relates to a device and method for jaw bone expansion, and more particularly, the invention relates to a device and method for creating traction on the upper jaw and dentition.

DESCRIPTION OF THE RELATED ART

Bones sometimes develop at different rates, leaving some bones disproportionately shorter than other bones. Alternatively, injury may leave a bone shorter than its original length. Such a condition may lead to difficulties in a patient's movement. For instance, a patient with a shortened tibia may need special shoes for assistance in walking. A small jaw can cause difficulties in chewing or breathing (obstructive sleep apnea). Moreover, deformations are often psychologically distressing to the patient, especially when the deformations occur in craniofacial bones.

One procedure for lengthening bones is referred to as osteosynthesis, osteogenesis, or osteodistraction. According to an osteogenesis procedure, an abnormally short bone is cut into two segments. The two segments are secured to a brace that permits the segments to be drawn apart. New bone then grows in the space between the separated bone segments, and eventually connects the two segments together into a lengthened bone. When the separated bone segments have been fully fused in this manner, the brace may be removed.

Many of the braces employed in osteogenesis procedures are simple mechanical bone fixation devices. Such devices have the shortcoming that they can not easily be adjusted once set. Other bracing devices are known, however, that allow the physician to periodically make adjustments in the brace during the lengthening procedure. For example, a physician may initially set such a brace so that a relatively short gap separates two bone segments. When new bone has filled in the gap between the two segments, the physician may adjust the brace such that the two bone segments are drawn farther apart, thereby creating a new gap. After bone has filled in the new gap between the two segments, the physician may once again draw the two segments farther apart. This procedure may be repeated as many times as necessary to lengthen the bone appropriately.

Conventional braces used for osteosynthesis are located external to the body. They attach to the bone through pins or screws. While these devices may achieve the desired end result of lengthening the deformed bone, they are unwieldy and unsightly, thereby preventing the user from engaging in many activities during the lengthening procedure. In addition, the mechanical advantage is less since there is a fulcrum effect on the long pins or screws. They also create unsightly scars where the pins extend through the skin. This scarring is particularly undesirable when they are located on the face.

Implantable bone distraction devices are described in U.S. Pat. Nos. 5,885,289 and 5,807,382 for extending bones of the skull. The implantable devices achieve the desired result of lengthening without the traumatic scaring and visible plates of the external devices. However, the implantable devices do not connect the right and left sides of the skull together to achieve better stability and simultaneous distraction with a single device.

Accordingly, it would be desirable to provide a maxillary distraction device that is totally inside the mouth to prevent unsightly visible plates and scarring and is bilateral in nature connecting the right and left halves of the midface across the midline.

SUMMARY OF THE INVENTION

The present invention relates to a device for maxillary jawbone expansion which is configured for mounting within the mouth and connects the right and left halves of the mid face and skull.

In accordance with one aspect of the present invention, a maxillary distraction device includes of at least two implantable anchors configured to be inserted into the bones of the malar region, a facebow configured to be positioned entirely within the mouth and to connect to one of the anchors on a right side malar region and to one of the anchors on a left side malar region, two vertical distraction screws for expanding the facebow vertically, and two anterior/posterior distraction screws for expanding the facebow horizontally.

In accordance with an additional aspect of the present invention, a maxillary distraction device includes of at least two implantable anchors configured to be implanted in the maxillary bones of the skull on opposite sides of a midline of the skull, and a facebow having two posterior ends connectable to the implantable anchors and configured to extend from the anchors entirely within the mouth across the midline of the skull, the facebow having at least one expandable section for bone lengthening.

In accordance with a further aspect of the invention, a method of performing osteogenesis of the maxillary bones includes the steps of implanting anchors in the right and left side maxillary bones, connecting a facebow to the anchors wherein the facebow extends entirely within the mouth across a midline of the patient, and lengthening the facebow periodically to lengthen the maxillary bones. Preferably, the facebow lengthens the maxillary bones and teeth in all three planes of space simultaneously.

BRIEF DESCRIPTION OF THE DRAWING FIGURES

The invention will now be described in greater detail with reference to the preferred embodiments illustrated in the accompanying drawings, in which like elements bear like reference numerals, and wherein.

DETAILED DESCRIPTION OF THE INVENTION

Figure 1:
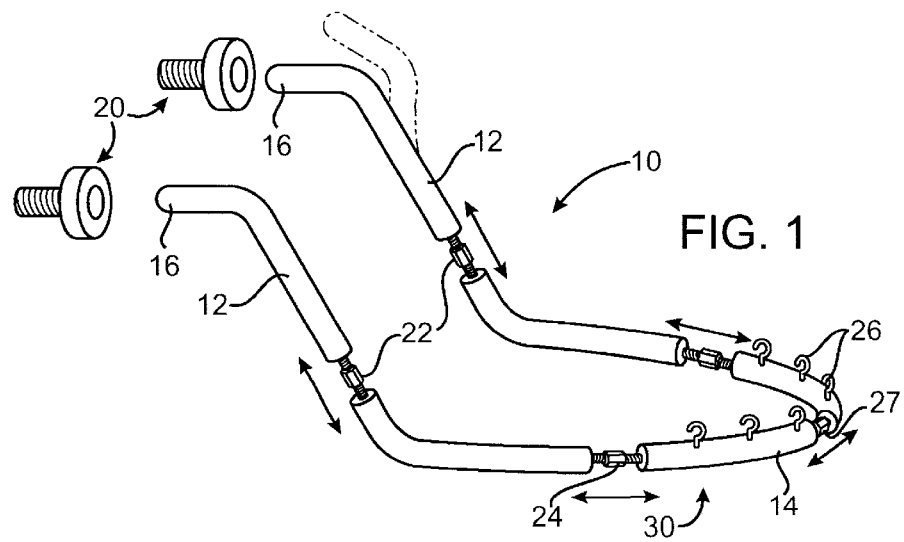
FIG. 1 is a perspective view of a maxillary distraction device according to a first embodiment of the invention.
Figure 2:
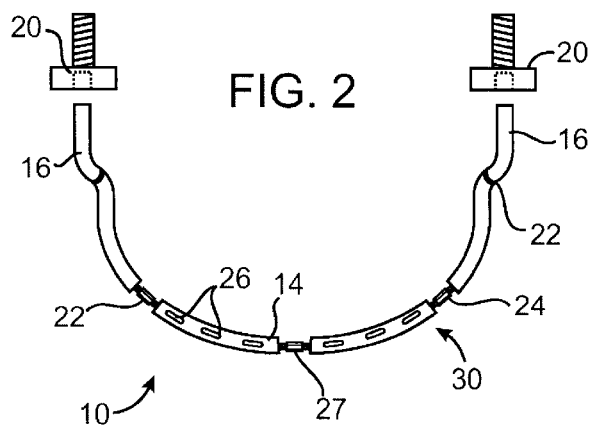
FIG. 2 is a top view of the maxillary distraction device of FIG. 1.
Figure 3:
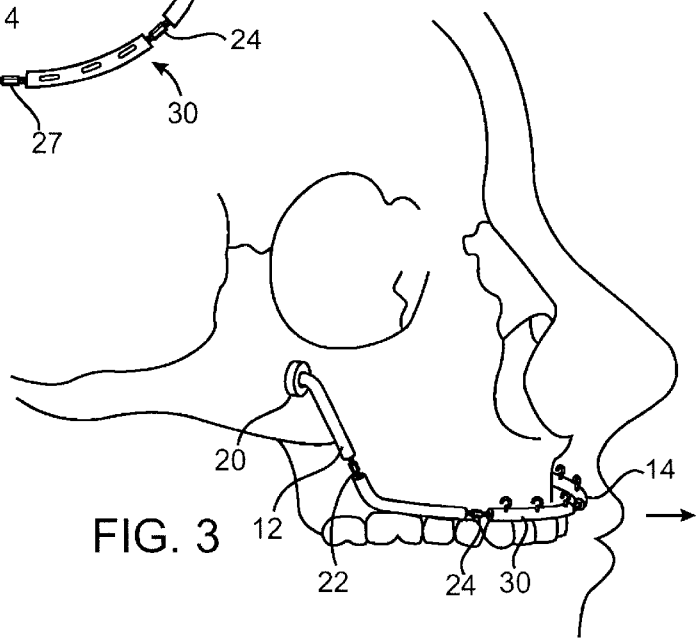
FIG. 3 is a perspective view of the maxillary distraction device of FIG. 1 in use.

FIGS. 1–3 illustrate a first embodiment of a maxillary distraction device 10 for providing anterior traction on the maxilla and midface. Distraction devices, such as those shown and described herein are generally used to lengthen bones to correct abnormalities and after facial fractures and injuries. The distraction device 10 of FIG. 1 includes two anchors 20 and a facebow 30. The facebow 30 includes two generally vertical posterior legs 12 connected to opposite ends of a substantially horizontal U-shaped anterior portion 14. The posterior legs 12 each have a free end 16 which is removably connectable to the implantable anchors 20. The implantable anchors 20 are in the form of large bone screws or other implants configured to be implanted into the maxillary bones at the malar region of the skull with the free ends or heads of the screws positioned within the mouth.

The implantable anchors 20 provide a fixation of the posterior ends of the facebow 30 to the skull while the anterior portion 14 of the facebow is fixed to the teeth or to the maxillary bone. The anterior U-shaped portion 14 is provided with one or more hooks 26. The hooks 26 are connected by orthodontic brackets and wires in a known manner to the teeth, or by plates, screws and/or wires to the maxillary bone. Preferably, the anterior portion 14 is connected to the teeth or bone on both sides of a midline of the skull.

The distraction device 10 of FIG. 1 includes two vertical distraction screws 22, one on each of the posterior legs 12, two horizontal anterior/posterior distraction screws 24 on the anterior portion 14, and a transverse distraction screw 27 at about the midline of the anterior portion. The distraction screws 22, 24, 27 allow the anterior and posterior portions of the facebow to be expanded and contracted in length to provide an initial fit and to subsequently provide the desired distraction. The use of two distraction screws 22, 24 on each side of a midline of the device allows the distraction to be controlled to achieve a desired amount of vertical and horizontal distraction which may be different for each side of the midline. The transverse distraction screw 27 allows the maxilla to be distracted transversely. The distraction screws 22, 24, 27 allow lengthening of the facebow 30 in three dimensions or three planes simultaneously. Expansion of the facebow by the distraction screws 22, 24, 27 is performed while the facebow remains in the patient's mouth and connected by the anchors 20 to the malar region and connected by the hooks 26 to the maxillary teeth and/or bones.

The distraction screws 22, 24, 27 may be any distraction mechanism which allows the axial expansion of the tubes of the facebow 30. The distraction screws 22, 24, 27 shown in FIGS. 1–3 include a central nut and a threaded screw extending from each side of the nut which are threaded into the tubes of the facebow. Rotation of the nut causes corresponding lengthening or shortening of the tubes of the facebow.

As shown in FIGS. 1–3, the anterior U-shaped portion 14 is curved to conform to the exterior of the teeth so that the anterior portion of the facebow 30 can be positioned within the mouth of the patient between the gums/teeth and the upper lip. The hooks 26 are preferably positioned on an upper surface of the U-shaped portion 14 for connection to orthodontics on the teeth or implants in the mouth without irritation to the mouth. The posterior legs 12 are initially arranged at an angle of about 80° to about 120° with respect to the anterior portion 14 and may be modified. The posterior legs 12 may be bent by the physician, as shown by the hidden lines in FIG. 1, to fit the particular patient.

Figure 4:
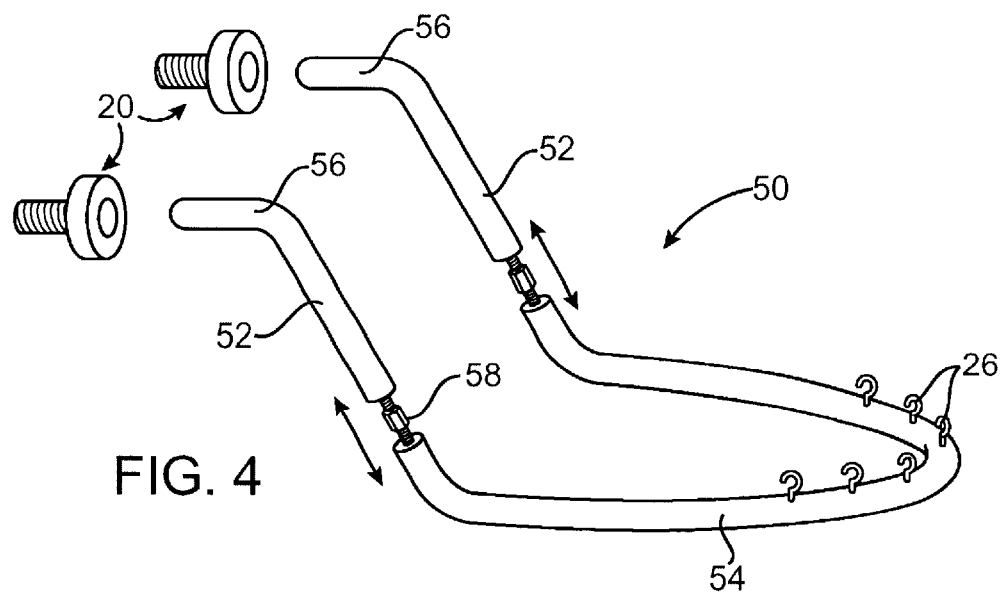
FIG. 4 is a perspective view of a maxillary distraction device according to a second embodiment.
Figure 5:
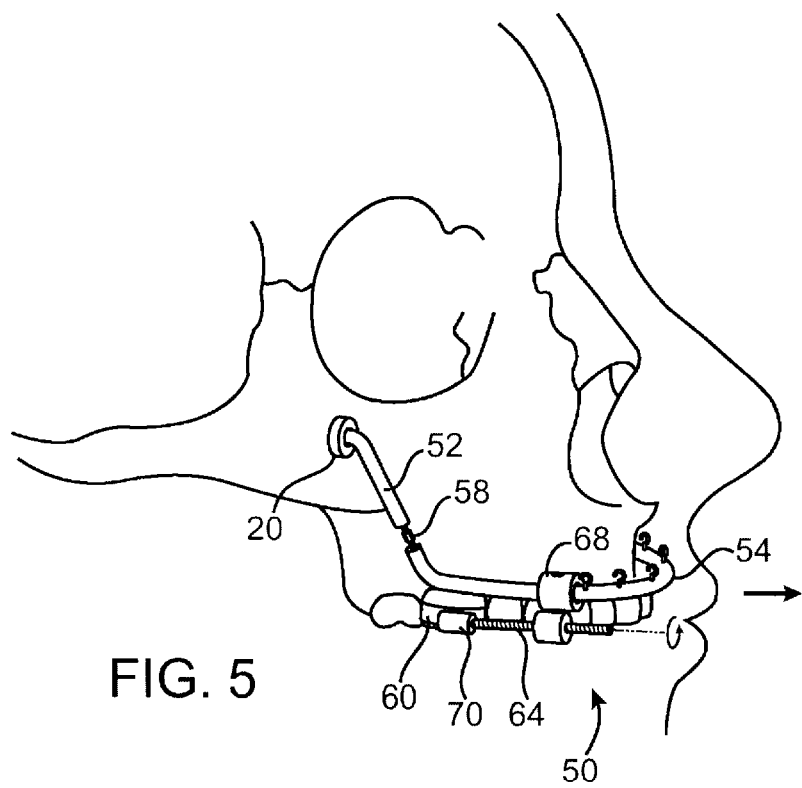
FIG. 5 is a perspective view of the maxillary distraction device of FIG. 4 in use.
Figure 6:
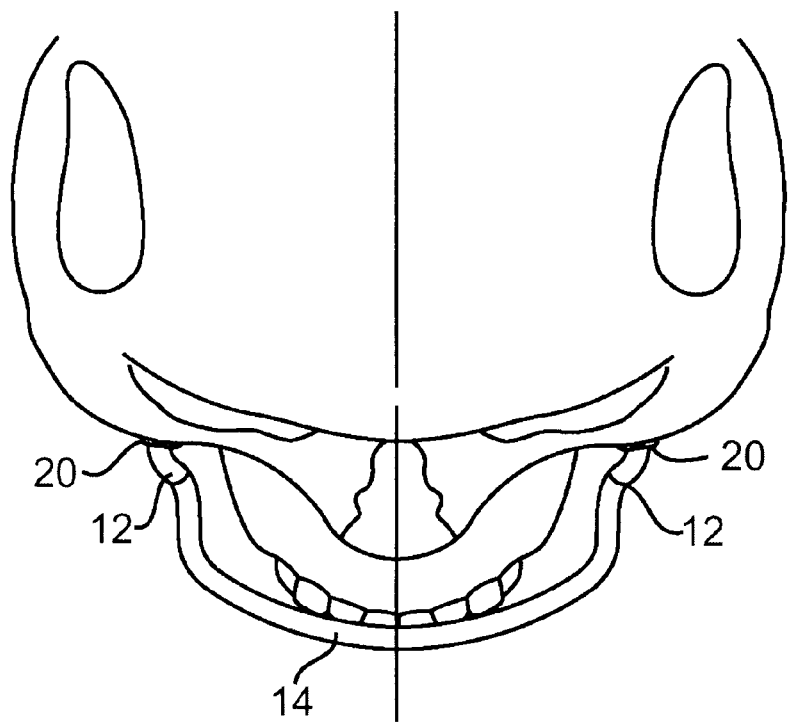
FIG. 6 is a top view of the maxillary distraction device of FIGS. 1 and 4 in use.
Figure 7:
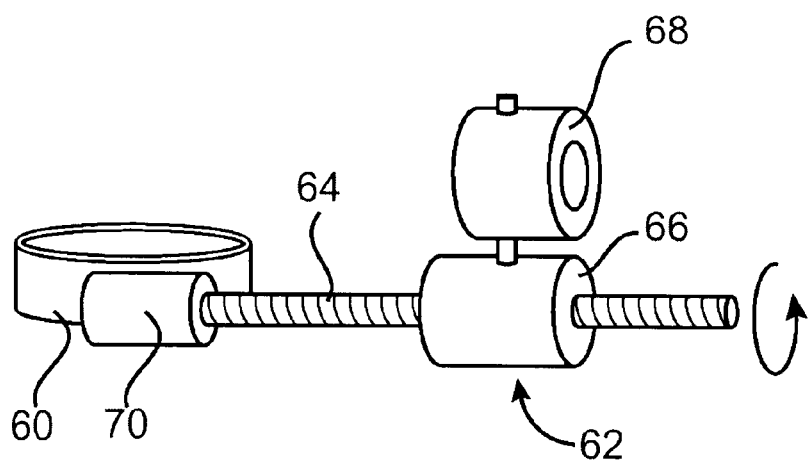
FIG. 7 is a perspective view of an orthodontic bracket connection device for use with the maxillary distraction device of FIG. 4.

FIGS. 4–7 illustrate an alternative embodiment of a distraction device 50 according to the present invention in which an orthodontic anchor and expandable connection member shown in FIG. 7 provide horizontal distraction. As shown in FIG. 4, the distraction device 50 includes two generally vertical posterior legs 52 connected to opposite ends of a substantially horizontal U-shaped anterior portion 54. The posterior legs 52 each have a free end 56 which is removably connectable to an implantable anchor 20 and a distraction screw 58, as in the embodiment of FIG. 1. The implantable anchors 20 provide a fixation of the posterior ends of the distraction device to the maxillary bones of the skull while the anterior portion of the distraction device is fixed to the teeth by an orthodontic band 60 and expandable connector 62 on each side (FIG. 7). The orthodontic bands 60 are connected in a known manner to two teeth, preferably molars, on opposite sides of a midline of the skull. The distraction device 50 of FIGS. 4–7 may also include a transverse distraction screw as shown in the embodiment of FIG. 1.

The expandable connector 62, as shown in FIG. 7, includes a threaded rod 64, an internally threaded nut 66 movable on the rod, and a clamping member 68 to attach to the anterior portion 54 of the distraction device 60. The rotatable rod 64 is connected to the orthodontic band 60 by a rotatable connector 70. To provide horizontal distraction, the end of the rod 64 is grasped and rotated in the rotatable connector 70 causing the threaded nut 66 to move along the rod. Lengthening of a distance between the band 60 and the nut 66 creates the desired distraction.

Figure 8:
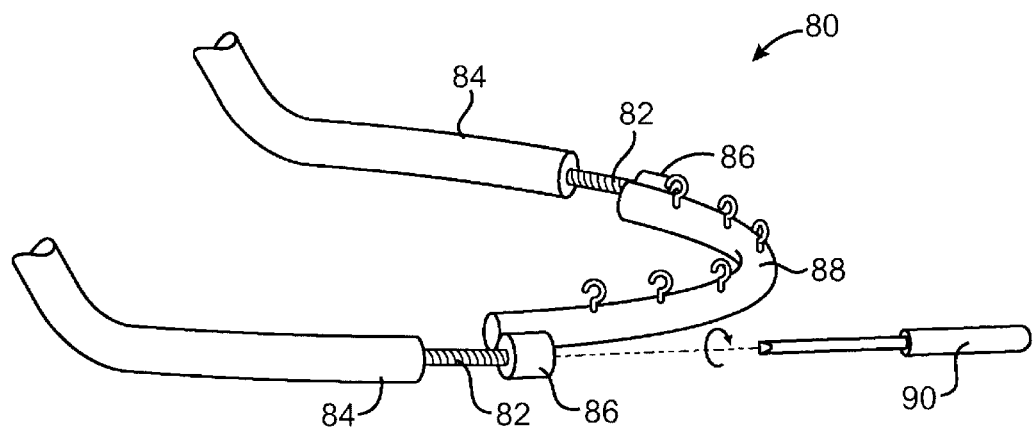
FIG. 8 is a perspective view of a portion of a maxillary distraction device according to an alternative embodiment.
Figure 9:
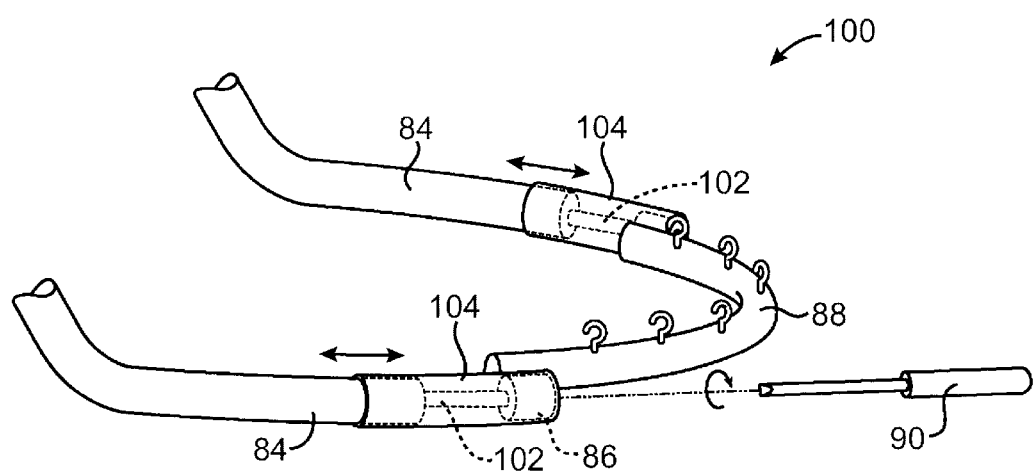
FIG. 9 is a perspective view of a portion of a maxillary distraction device according to a further alternative embodiment.

FIGS. 8 and 9 illustrate two alternative embodiments of the distraction screws of the present invention. A facebow 80 of FIG. 8 includes horizontal distraction screws 82 which are threaded into the ends side tubes 84. The distraction screws 82 are rotatably received in rotatable connectors 86 which are fixed on an anterior U-shaped portion 88 of the facebow 80. Rotation of the distraction screws 82 by the screwdriver 90 causes lengthening or shortening of the facebow 80.

In the embodiment of FIG. 9, a facebow 100 is formed with the anterior distraction screws 102. The distraction screws 102 are each covered by a tube or sleeve 104 which is connected to the rotatable connector 86 and is slidable over the side tube 84. The distraction screws illustrated in the various embodiments of the present invention are merely examples of the types of distraction screws which may be employed in this bilateral maxillary distraction device. The locations and numbers of distraction screws may be varied without departing from the present invention.

While the invention has been described in detail with reference to the preferred embodiments thereof, it will be apparent to one skilled in the art that various changes and modifications can be made and equivalents employed, without departing from the present invention.

What is claimed is:

1. A maxillary distraction device comprising:
   at least two implantable anchors configured to be inserted into the bones of the malar region;
   a facebow configured to be positioned entirely within the mouth and to connect to one of the anchors on a right side malar region and to one of the anchors on a left side malar region, two vertical distraction screws for expanding the facebow vertically, and two anterior/posterior distraction screws for expanding the facebow horizontally.

2. The device of claim 1, wherein the implantable anchors are bone screws.

3. The device of claim 1, wherein the vertical distraction screws are within two substantially vertical posterior legs of the facebow.

4. The device of claim 1, wherein the anterior/posterior distraction screws are within two substantially horizontal anterior legs of the facebow.

5. The device of claim 4, wherein the two substantially horizontal anterior legs of the facebow are connected at an anterior portion of the facebow.

6. The device of claim 1, wherein the facebow includes a plurality of hooks for fixation.

7. The device of claim 1, further comprising at least two orthodontic brackets connected to the facebow, wherein the anterior/posterior distraction screws are rotatable to extend and contract a connection between the orthodontic brackets and the facebow.

8. The device of claim 1, wherein the anchors are configured to be implanted in the bone with a connecting portion of the anchors extending through the gum tissues.

9. The device of claim 1, wherein the distraction screws are configured to be rotated to provide distraction while the facebow is connected to the implanted anchors.

10. The device of claim 1, further comprising a transverse distraction screw for expanding the facebow transversely.

11. A maxillary distraction device comprising:
at least two implantable anchors configured to be implanted in the maxillary bones of the skull on opposite sides of a midline of the skull; and
a facebow having two posterior ends connectable to the implantable anchors and configured to extend from the anchors entirely within the mouth across the midline of the skull, the facebow having at least one expandable section for bone lengthening.

12. The device of claim 11, wherein the at least one expandable section of the facebow comprises two vertical expandable sections on opposite sides of a midline of the distraction device.

13. The device of claim 12, wherein the at least one expandable section of the facebow further comprises two anterior/posterior expandable sections on opposite sides of the midline of the distraction device.

14. The device of claim 13, wherein the at least one expandable section of the facebow further comprises a transverse expandable section substantially at the midline of the distraction device.

15. The device of claim 12, further comprising at least two orthodontic brackets connected to the distraction device by a connector segment having an expansion screw configured to extend and contract a connection between the orthodontic brackets and the facebow.

16. The device of claim 1, further comprising a fixing mechanism for fixing an anterior portion of the facebow to the teeth or anterior bones of skull.

17. A method of performing osteogensis of the maxillary bones, the method comprising:
implanting anchors in the right and left side maxillary bones;
connecting a facebow to the anchors wherein the facebow extends entirely within the mouth across a midline of the patient; and
lengthening the facebow periodically to lengthen the maxillary bones.

18. The method of claim 17, wherein the step of lengthening is performed while the facebow is connected to the implanted anchors.

19. The method of claim 17, further comprising a step of fixing an anterior portion of the facebow to the teeth or bone at an anterior location and wherein the anchors are implanted at a posterior location.

20. The method of claim 17, wherein the anterior portion of the facebow is fixed to the teeth by an orthodontic band.

21. The method of claim 17, wherein the step of lengthening the facebow is performed by providing both substantially vertical and substantially horizontal distraction.

22. The method of claim 21, wherein the step of lengthening the facebow is performed by further providing transverse distraction.

* * * * *